US005841882A

United States Patent [19]
Celeski

[11] Patent Number: 5,841,882
[45] Date of Patent: Nov. 24, 1998

[54] AUTOMATIC PROCESS FOR THE MACERAL ANALYSIS AND THE DETERMINATION OF THE REFLECTANCE OF VITRINITE IN COALS

[75] Inventor: Jean-Claude Celeski, Fos-Sur-Mer, France

[73] Assignee: Sollac, Puteaux, France

[21] Appl. No.: 355,233

[22] Filed: Dec. 9, 1994

[30] Foreign Application Priority Data

Dec. 10, 1993 [FR] France .................................. 93 14884

[51] Int. Cl.$^6$ ...................................................... G06F 9/00
[52] U.S. Cl. ........................................... 382/109; 382/272
[58] Field of Search ....................... 348/79, 80; 364/556, 364/497, 498, 550, 555; 382/100, 108, 109, 141, 174, 192, 201, 206, 272, 171, 172

[56] References Cited

U.S. PATENT DOCUMENTS

| | | |
|---|---|---|
| 4,030,837 | 6/1977 | Kojima et al. . |
| 4,617,682 | 10/1986 | Mori et al. . |
| 4,959,549 | 9/1990 | Haub et al. ........................... 250/461.1 |
| 5,129,268 | 7/1992 | Uesugi et al. .......................... 73/865.5 |
| 5,155,546 | 10/1992 | Balsam et al. . |
| 5,157,541 | 10/1992 | Schildkraut et al. ................... 359/276 |
| 5,303,310 | 4/1994 | Grove ........................................... 382/8 |
| 5,396,260 | 3/1995 | Adel et al. ................................. 345/91 |

FOREIGN PATENT DOCUMENTS

| | | |
|---|---|---|
| 2649794 | 1/1991 | France . |
| 83 00556 | 2/1983 | WIPO . |

OTHER PUBLICATIONS

Mori, et al: "Automatic Measurement of Coke Microtectures", International Laboratory, vol. 15, No. 7, Sep. 1985, pp. 78–80.

*Primary Examiner*—Joseph Mancuso
*Attorney, Agent, or Firm*—Cushman, Darby & Cushman

[57] ABSTRACT

A process for the maceral analysis of a sample of crushed coal coated with resin includes the steps of scanning the surface of the sample with a microscope and measuring the reflectance of the vitrinite. The process further includes the steps of forming a digitized image having gray levels for each field of the microscope and eliminating those fields having a high resin content. In those fields which are not eliminated, the distribution of gray levels and gradients are determined, a binary image is formed by thresholding the gray gradients to determine zones of vitrinite, the distribution of the gray levels of the obtained zones of vitrinite are then determined and the reflectance of the vitrinite is calculated.

8 Claims, 6 Drawing Sheets

Gray levels measured by image analysis

AUTOMATIC PROCESS FOR THE MACERAL ANALYSIS AND THE DETERMINATION OF THE REFLECTANCE OF VITRINITE IN COALS

FIELD OF THE INVENTION

The invention relates to a process for characterizing coal for the purpose of determining their vitrinite content.

DESCRIPTION OF THE RELATED ART

Models for preparing and predicting the quality of coke employ certain parameters deduced from the petrographic analysis, such as the reflectance and the proportion or content of vitrinite which is the principal constituent of coal. The values of these two parameters permit evaluating the coking properties of the coal.

Coal entering into the coke paste have a reflectance vitrinite reflectance which varies from 0.5% to 1.7%, the proportion of vitrinite being between 40% and 85%. Coal having a high coking power is characterized by a vitrinite reflectance between 1.1% and 1.3% and by a high vitrinite content.

The supplies of coal are inspected or monitored in a systematic manner to check the conformity and the regularity of the quality of the raw material to thereby enable coke of constant quality to be produced and to evaluate the cost of the coal.

Quality control of coal is currently effected manually. To do this, a sample of crushed coal coated with a resin is polished and placed in an optical microscope having magnification of, for example, 300.

The microscope is equipped with a reflectometer which is calibrated against a standard surface having a known reflectance.

The reflectance of the sample is measured by scanning it along a path forming an even grid or a rectangular pattern. The precision of the quality control of the coal is a function of the number of measurements taken.

The standard defined by petrographs prescribes 200 measurements for a conventional coal sample. When it is desired to reveal either a presence of a pollutive element or composition, it is necessary to sample 300 or 400 specimens.

Maceral analysis involves determining the proportions of the principal constituents by scanning the sample as described above. The operator defines the maceral which is located at the centre of the cross hairs and counts the frequency of appearance of this maceral during the scanning. Industry standards prescribes 500 specimens for estimating the proportion of the different macerals, namely essentially exinite, vitrinite, fusinite, semi-fusinite and inertinite.

The manual method for measuring the mean reflectance and effecting the maceral analysis requires from three to six hours of analysis depending on the difficulty presented by the coal.

This analyzing time is long and requires the permanent presence of the operator; Further, the method is exacting and precision of the measurements is low.

SUMMARY OF THE INVENTION

A purpose of the present invention is to automate the process of determining the value of the reflectance of the vitrinite and effecting the maceral analysis with an improved precision and a shorter measuring time.

The invention therefore provides a process for the maceral analysis of coal for the purpose of determining its vitrinite content, by employing a sample of crushed coal coated with resin, scanning the surface of the sample with a microscope by displacing the sample so as to obtain successive fields in the microscope and measuring the reflectance of the vitrinite. The method includes the following steps:

producing for each field of the microscope a digitized image having gray levels;

effecting on each image a threshold measure for eliminating fields containing a quantity of resin higher than a given threshold (80%);and;

effecting the following analysis for each non-eliminated field:
 a) determining the distribution of the gray levels;
 b) determining the gradients of the gray levels;
 c) producing a binary image by thresholding gray gradients in such manner as to determine zones of vitrinite;
 d) determining the distribution of the gray levels or the densitometry of the zones of vitrinite obtained, and
 e) calculating the reflectance of the vitrinite.

According to another feature of the invention, the reflectance of the vitrinite is calculated by determining the mean gray level for all of the zones of vitrinite of the sample.

According to a further feature of the invention, the reflectance of the vitrinite is calculated by determining the mean gray level of each zone of vitrinite.

BRIEF DESCRIPTION OF THE DRAWINGS

Further features and advantages of the invention will be apparent from the following description of an embodiment of the invention with reference to the accompanying drawings in which.

DESCRIPTION OF THE PREFERRED EMBODIMENTS

Figure 1:
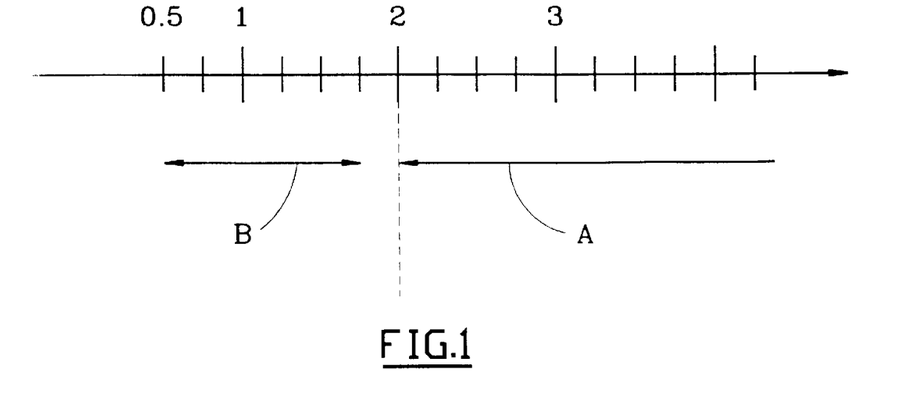
FIG. 1 is a linear diagram of the reflectance of a sample of coal.

FIG. 1 shows a linear diagram of the reflectance measured on a sample of coal. When the reflectance is higher than 2

(in the zone A) it concerns an anthracite, i.e. a high ranking coal which cannot be coked.

Vitrinite is light in color and presents large plates having a reflectance located in zone B, i.e. between 0.5 and 1.7 for coking coal. This coal is useful for making coke.

The following table illustrates a classification of coals according to their reflectance.

| CLASSIFICATION OF COALS | | | | |
|---|---|---|---|---|
| Peat | Lignite | Long-flaming Coals | Coking Coals | Anthracites |
| | | | Reflectance of the vitrinite | |
| ← very low mean R | | | 0.5       1.7 → | very high mean R |

Coking coal is composed of the following elements, which have been tested in increasing order of reflectance: exinite, vitrinite, semi-fusinite, fusinite and inertinite.

In the known manual maceral analysis of coal, a microscope equipped with a calibrated reflectometer is used. In this process, the determination of the proportion of the different macerals is based on the experience of the operator who notes at the centre of the cross hairs the nature of the maceral. The operator is sometimes assisted in making a punctual measure of the reflectance for distinguishing the semi-fusinites from the vitrinite.

The reflectance is the lowest for the exinite which corresponds to a proportion of 0 to 3% by weight. In increasing order vitrinite accounts for between 45% and 85% by weight. semi-fusinite and fusinite together correspond to a proportion of between 15% and 45% and inertinite, having a very high reflectance generally accounts for less than 10%.

Figure 2:
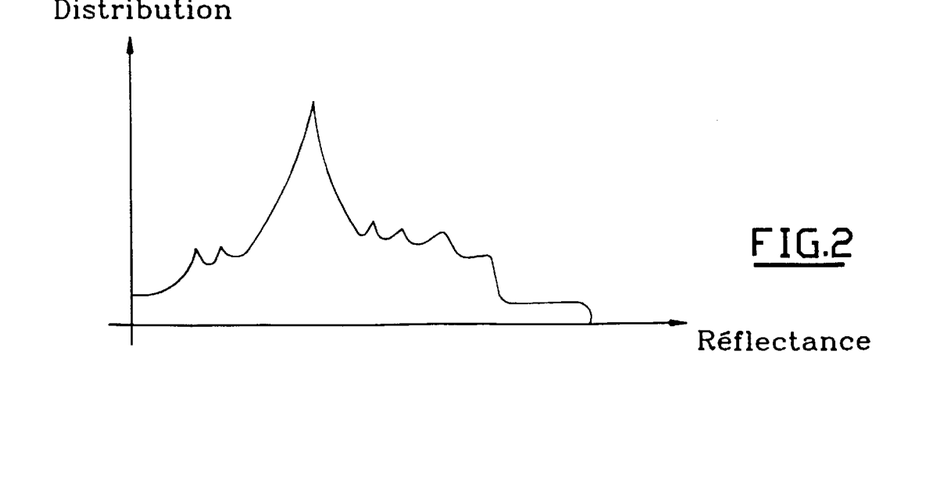
FIG. 2 is a diagram of the distribution of typical reflectance.

FIG. 2 shows a diagram indicating the distribution or the frequency versus the measured reflectance. This curve permits measuring the quality of the coal and determining the vitrinite content percentage.

The present invention concerns an automatic process for maceral analysis which is based on the observation of a sample prepared under the same conditions as used in the known manual process.

In this process, a microscope is also used and preliminary calibrating operations are effected. First of all, by employing a standard surface with known reflectance the lighting of the microscope is adjusted manually.

Further, the value of a coefficient K for each image point of the digitized image is calculated; this coefficient K permits effecting an automatic correction of the homogeneity so as to obtain always the same mean gray value (densitometry) on the standard surface.

The maceral composition is calculated in the following manner:

$$\% \text{ vitrinite} = \frac{\text{number of points found in the vitrinite}}{\text{total number of points (500)}}$$

similar equations can be formed to determine the composition of the other macerals.

Indeed, the image acquired on an optical microscope with the aid of a video camera often has a defect of homogeneity which is related to the regulation of the lighting or to the camera.

In order to correct this homogeneity, there is therefore employed a reference image acquired under the same working conditions on the standard surface which is uniform in gray levels.

This image integrates the different defects of uniformity; by means of these different values of gray levels, a matrix of the size of the images to be processed is constructed by calculating the coefficient of correction K for each of the image points from the following equation:

$$K_{ij} = \frac{GL_{max}}{GL_{ij}}$$

in which $GL_{ij}$ is the gray level at point $_{ij}$ and $GL_{max}$ is the maximum gray level of the image.

The correction will consist in modifying the gray level of each image point proportionally to its coefficient K in accordance with the following calculation mode:

$$\text{CORRECTED IMAGE}_{ij} = \frac{K_{ij} \text{ IMAGE}_{ij}}{SUP(K_{ij})}$$

in which $\text{IMAGE}_{ij}$ is the image to be processed and SUP $(K_{ij})$ the maximum value of the coefficients K.

This correction is particularly important in the framework of this application since the reflectance of one of the constituents is characterized by measuring and showing small variations in the reflectance.

The purpose of the homogeneity correction is to avoid obtaining for the same zone of the sample different values of the reflectance in accordance with the position in the field of the camera.

After these preliminary calibrating operations, the operator places the sample to be analyzed in position and enters the references of this sample in a data storage device.

The rest of the analyzing process is completely automatic. The different operations are the following:

displacement of the plate supporting the sample;

automatic focusing;

acquisition of an image;

processing the image;

densitometric measurements.

The last operation is carried out only for the non-eliminated images.

The acquisition of the image is achieved with a microscope equipped with a camera providing an image digitized in gray levels. One may for example employ a digitized image in which the gray levels vary from 0 to 255, i.e. they are encoded on an octet.

The first operation of the automatic processing of the image is intended to eliminate the images corresponding to fields of the microscope in which the proportion of resin is very high, for example higher than 80%.

To this end, a threshold process is employed by analyzing the image point by point and creating a binary image in which each pixel can only assume a value of 0 or 1.

This threshold operation is based on the fact that the gray levels corresponding to the resin are rather similar on each field and each sample; the observation of a large number of operations has permitted fixing the range of gray levels corresponding to the resin between 0 and 70 in the case where the image is encoded on an octet, i.e. when the gray levels vary between 0 and 255.

In this case a binary image is created in which, for each image point, the value is equal to 1 if the reflectance is lower than or equal to 70 and to 0 if this reflectance is higher than 70.

The proportion of coating resin is then determined, i.e. the ratio of the sum of the binary values of all of the image points to the total number of these points. If this proportion is higher than or equal to 80%, the corresponding image is eliminated and the sample is shifted for the acquisition of another field.

For all the non-eliminated fields or images, the following steps are then effected.

First, the homogeneity is corrected by applying the correction factor K, as defined above, to each image point.

The distribution of the gray levels is then measured to obtain an overall densitometry of the coal.

Figure 3:
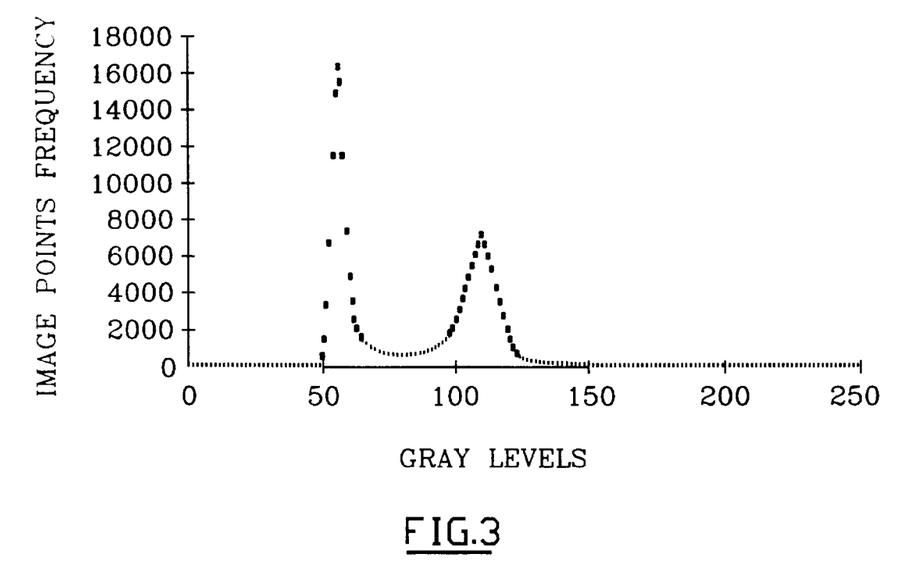
FIG. 3 is a diagram of the densitometry on an image digitized in gray levels with correction of the effect of the porosity of the resin.

The densitometry is defined as being the distribution of the gray levels in an image and, more precisely, it represents the number of image points corresponding to each gray level. The curve shown in FIG. 3 represents an example of the distribution of the densitometry on an image digitized in gray levels. The values of the gray levels are plotted as abscissae and the frequency of the appearance of the image points having the corresponding gray level is plotted as ordinates.

The gray gradients are then analyzed. Indeed, vitrinite is the component of coal, which has the greatest homogeneity, i.e. the largest areas presenting very little variations in gray level.

This is why the revealing of the homogeneous zones of vitrinite is based on the analysis of the gray gradients of the digitized image which had been subjected to the homogeneity correction.

The gradient of a digitized image is represented by the formula:

$$g(x) = \frac{1}{n} \sum_{i=1}^{n} f(x) - f(x_i)$$

in which n is the number of points close to the considered image point, f(x) is the gray level at the considered image point and $f(x_i)$ is the value of the gray level for each of the neighbouring points.

The result of the filtering by analysis of the gradients is constituted by a new digitized image whose gray levels correspond to the measured variations between each point and its neighbours.

A zone where each point has the same gray value (perfect uniformity) will give a gradient value equal to 0 for each image point. The largest gradient which could exist in an image encoded on an octet is therefore equal to 255 which corresponds to an image point whose gray value is equal to 0 and for which the neighbouring points have a gray value to 255.

In the case of a square frame, each image point has eight neighbouring points.

Analysis of different coal has permitted the critical value of the gradient to be determined which characterizes the gray uniformity of the vitrinite under the measuring conditions. This value is equal to 20 for a digitized image encoded on an octet.

Figure 4A:
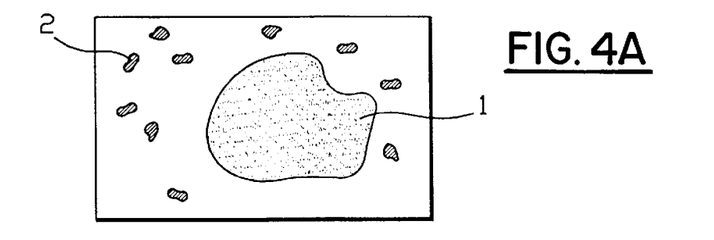
FIG. 4 illustrates a filtering operation on the images obtained.
Figure 4B:
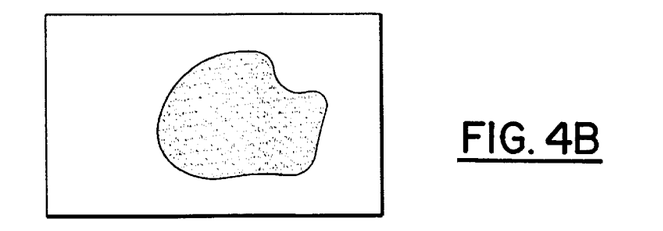

A binary image is then obtained by thresholding the gray levels of the gradients. If the value of the gradient of an image point is higher than 20, its binary value is set 1, otherwise this binary value is set to 0. A binary image as shown in the upper part of FIG. 4 is obtained. This binary image represents all of the points which have a gradient value between 21 and 255. A homogeneous zone 1 of large area and zones 2 of very small areas can be seen.

The morphological operations such as erosion are procedures known in image analyzing systems. They are based on the principles of mathematical morphology.

A morphological filtering by takes place which eliminates the small zones and keeps the large zones of vitrinite. The filtering is effected by erosion so as to retain only the homogeneous vitrinite zones with large areas. A binary image such as that shown in the lower part of FIG. 4 is thus obtained.

To determine the binary image from the gradients, a gradient value equal to 18 may be for example chosen; if the gradient of an image point is lower than or equal to this value, its binary value is 1; if the gradient of an image point is higher than this value, its binary value is 0.

The distribution of gray levels of the large zones of vitrinite are then measured. For this purpose the initial digitized image after correction of the homogeneity is used—the measure being effected only on the zones of vitrinite which were defined hereinbefore.

To obtain thee reflectance of vitrinite, two methods may be used. In the first method the mean gray levels for all of the zones of vitrinite of the sample are measured, and in the second method, the mean gray level of each zone is determined.

When a mixture or a pollution is concerned, the second method permits easily revealing the presence of two coals. The measure of the mean gray level does not include an error provided the measure of each zone is weighted by a coefficient proportional to the area it occupies.

The measure of the reflectance of vitrinite and the maceral analysis are carried out simultaneously, the duration of the analysis being less than one hour.

Figure 9:
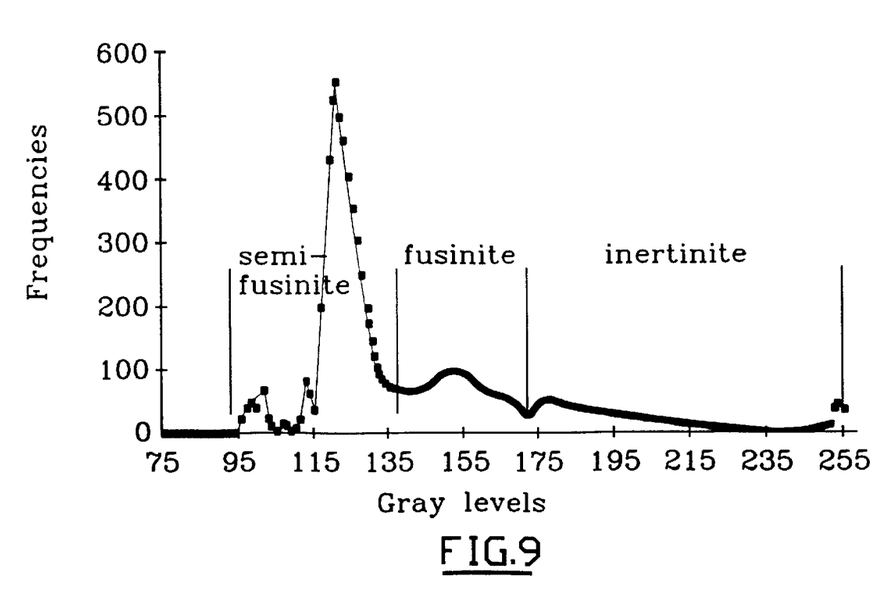
FIG. 9 is a distribution diagram revealing the other constituents of the coal.

The proportion of vitrinite is estimated from the integral of the distributions of the overall densitometry of the coal and of that of the vitrinite. After superimposition and by difference, the proportion of vitrinite is calculated. The proportion of the other constituents of the coal is estimated by analysis of the distribution without vitrinite, as illustrated in FIG. 9.

The different data obtained are recorded in data banks, which permits monitoring the quality of the coal employed in the fabrication of coke.

The applicant has effected comparisons between the results provided by the process according to the invention and those provided by the manual method of known type. The comparison of these two methods is illustrated in FIGS. 5 to 7.

Figure 5:
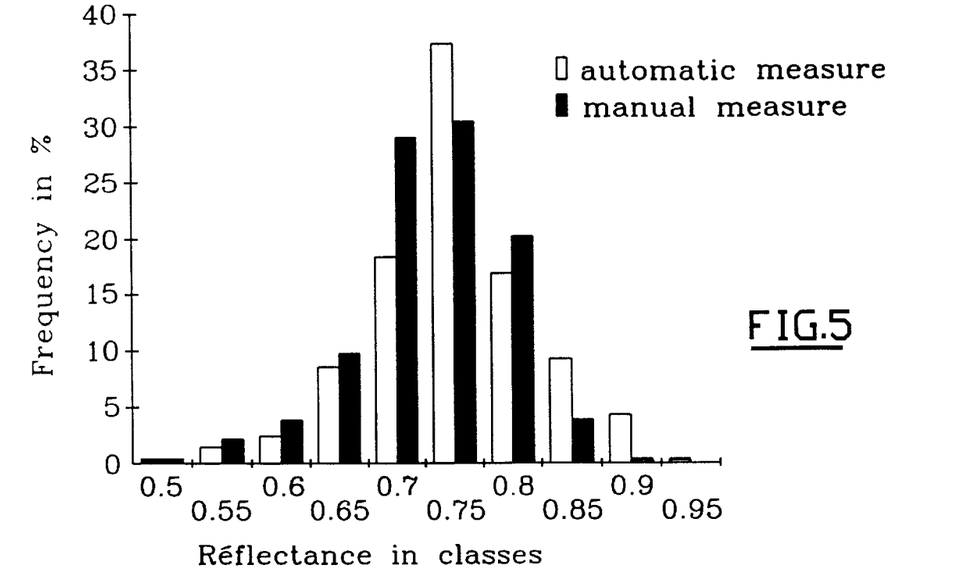
FIGS. 5 and 6 are distribution diagrams permitting a comparison of the results of the process according to the invention with results obtained by the manual process of known type.
Figure 6:
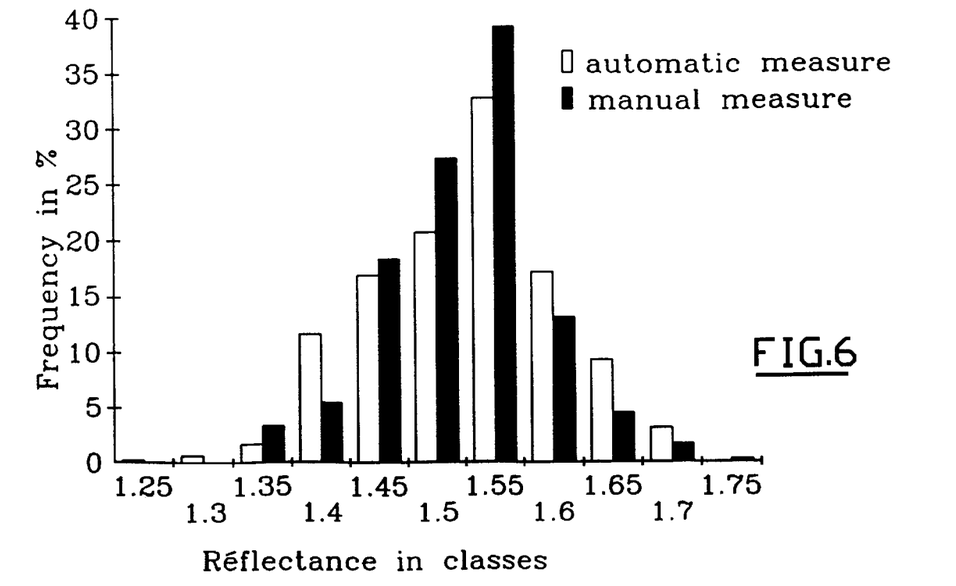

FIGS. 5 and 6 are curves of the distribution versus the reflectance put in the form of a histogram. The black bars correspond to the measurements made with the known manual method, and the white bars correspond to measurements according to the present invention. A very good correlation can be seen between the measures effected automatically and by the known manual method. FIG. 5 concerns a low ranking coal and FIG. 6 a coal of high rank.

Figure 7:
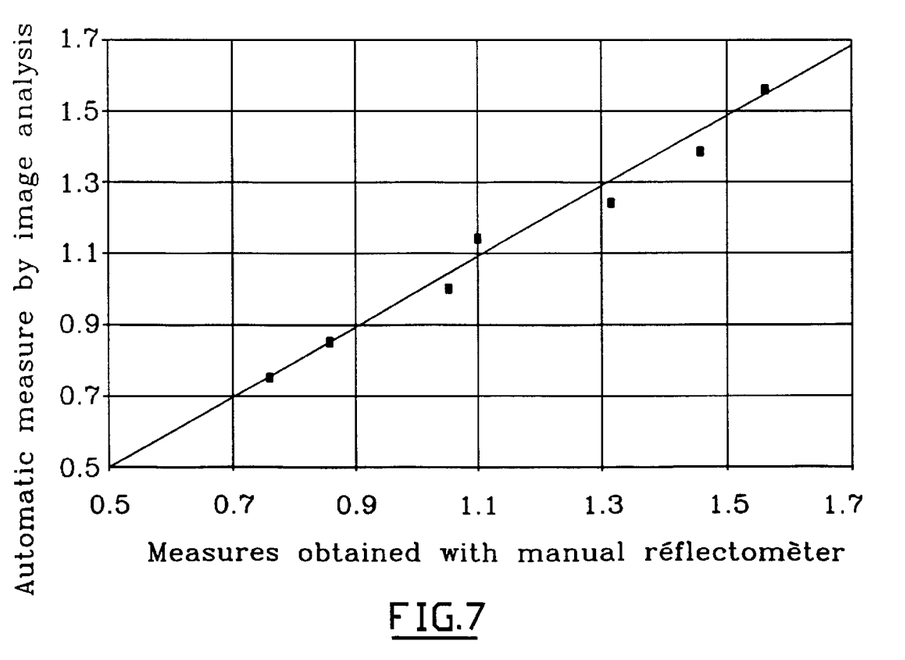
FIG. 7 is another diagram comparing the process according to the invention with the manual program of known type.

This correlation is illustrated in FIG. 7, in which the measurements of the reflectance of the vitrinite obtained by a manual method of known type are plotted as abscissa and the measurements obtained by the process according to the present invention are plotted as the ordinate.

Figure 10:
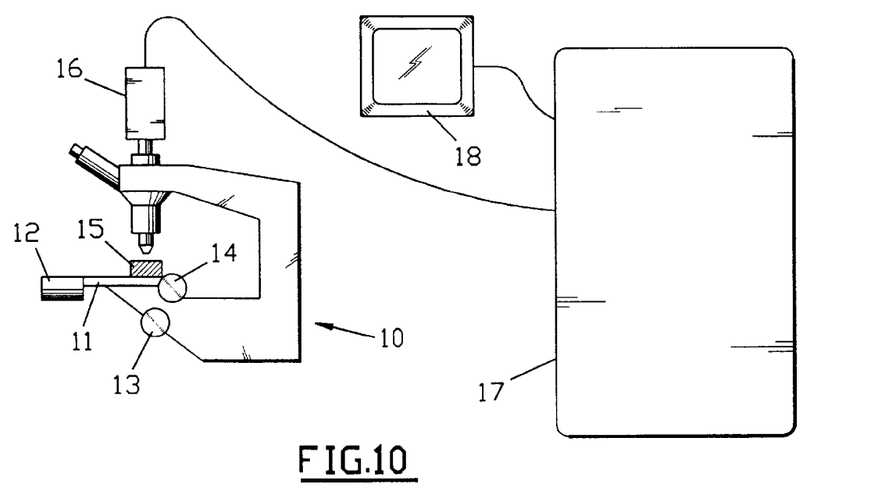
FIG. 10 is a diagrammatic representation of a device for carrying out the process according to the invention.

FIG. 10 represents diagrammatically a device for carrying out the process according to the invention. It comprises an optical reflected light microscope 10 equipped with a magnifying oil immersion objective lens 20. This microscope comprises a stage 11 which is movable along three axes (X, Y and Z) by means of motors 12, 13 and 14. This permits the programmed displacement of the sample and the automatic focusing. A camera 16 of the charge transfer type (CCD) employing points formed with a resolution of 550×740 image points is fixed on the microscope 10.

The images provided by the camera 6 are sent to a computer system 17 which comprises, in particular, a display device 18 and which controls the motors of the microscope 10.

Figure 11A:
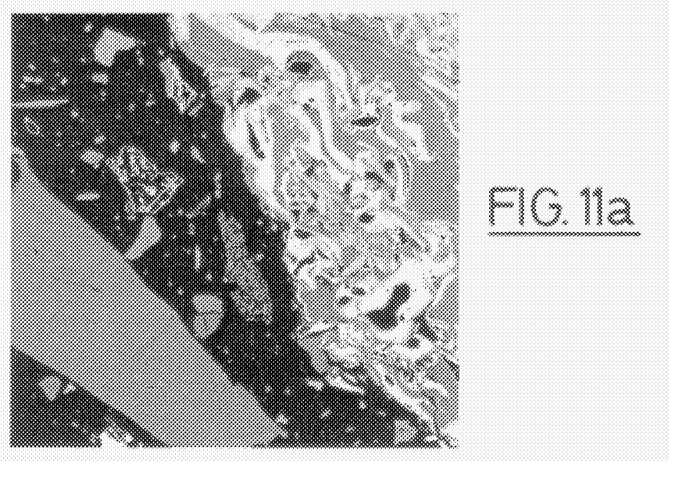
FIGS. 11A to 11C illustrate the treatment effected in the device of FIG. 10.
Figures 11B, 11C:
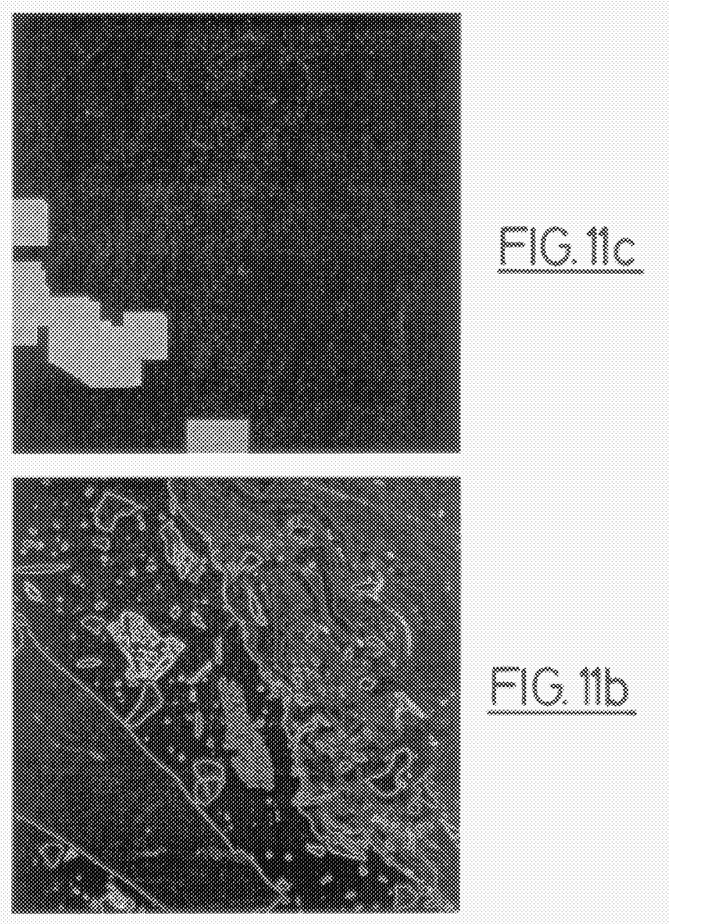

FIGS. 11A to 11C represent an example of the processing of an area of coal.

The interesting information in an area of coal is constituted by the whole of the image complementary to the coating resin shown in black in FIG. 11A.

This resin always has the same range of gray between 0 and 70. The effect of the porosity is eliminated in the following manner.

Bearing in mind this remark, there is defined an analyzing mask corresponding to the complementary of the image of the eroded resin of 2.2 $\mu$m. The purpose of this erosion is to eliminate the polishing defects (relief) observed on the edge of the resin and of the porosity. This defect generates gray levels which do not correspond to reality and no account is taken thereof by these means.

FIG. 3 shows the effect of this filtering on the distribution of the gray levels in a coal without the peak corresponding to the resin and to the porosity. All the densitometry measures (coal and vitrinite) are effected through this mask.

The areas of vitrinite are revealed in the following manner. The gray gradiants observed in this area of the coal are represented in FIG. 11B. It is already possible to predict the zones of greater homogeneity which are shown very dark since they have small gradients.

The thresholding of the gradients to a value higher than 20 permits obtaining a binary image ($BI_G$) of which the parts equal to 0 are the most homogeneous (FIG. 11B).

The reflectance domain of the vitrinite in coking coals is in the values GL of 80 and 190.

A binary mask ($BI_M$) is therefore constructed by solely taking into account this range of GL.

In this way the porosity, the resin and the inertinites are eliminated.

The areas of vitrinite are revealed by causing the image $BI_m$ to intersect with the complementary of the image $BI_G$, the resulting image being eroded by a structuring element of 25 $\mu$m and then dilated to the size of 20 $\mu$pm.

$$((\overline{BI}_G \cap BI_M) \ominus H_{25} \,\mu m) \oplus H_{20} \,\mu m$$

The result of these Boolean operations is represented in FIG. 11C.

Figure 8:
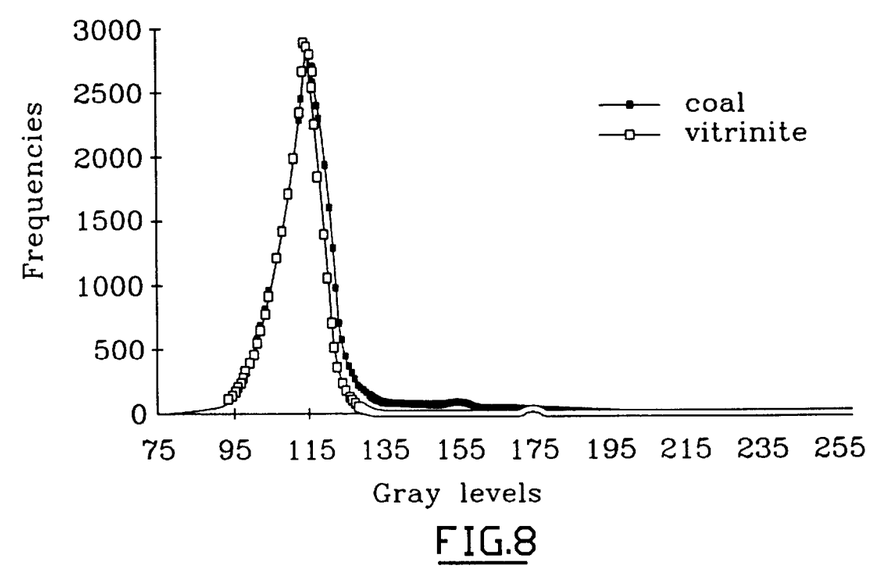
FIG. 8 is a distribution diagram in which there has been effected a correction of the effects of the porosity for measures obtained with the process according to the invention and with the manual process of known type.

FIGS. 8 and 9 illustrate the manner in which the composition of the sample of coal is determined.

When the densitometry determined on the whole of the sample is analyzed, it is impossible to indicate on the distribution the part of the gray levels corresponding to the vitrinite.

By discriminating the vitrinite from the coal by the gradient and the morphological filter it is therefore possible to measure the distribution of the gray levels of the vitrinite without bias. By deducing the distribution of the gray levels of the vitrinite from that of the coal, the part of the other macerals can be estimated.

The integral of the densitometry of the coal represents the sum of the macerals. The integral of the densitometry of the vitrinite represents the vitrinite part and the integral of the difference of these two distributions gives the part of the other macerals and permits in particular estimating the proportion of the inerts.

Figure 12:
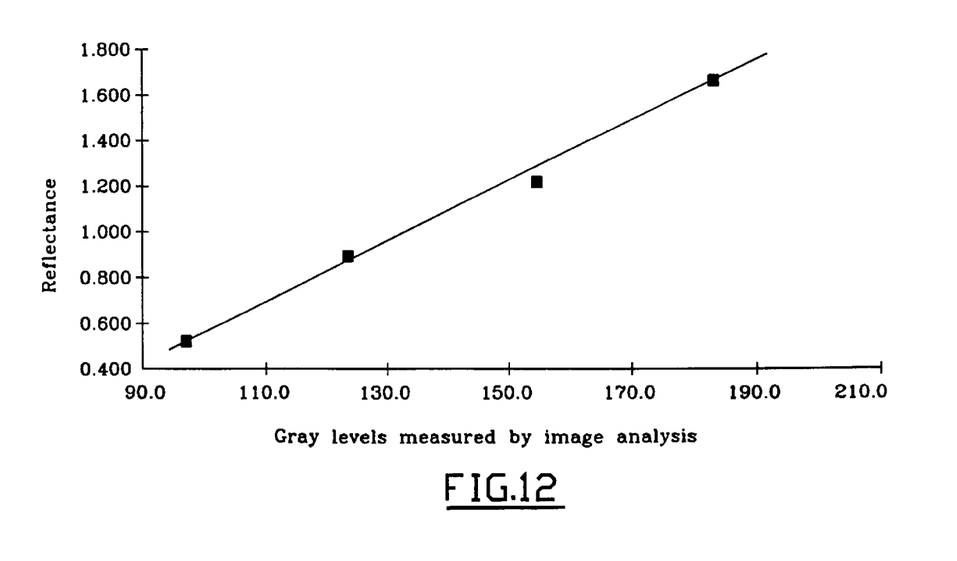
FIG. 12 is a calibrating curve which represents the correlation between the known reflectance of standard surfaces and the mean gray level.

FIG. 12 represents the calibrating curve, i.e. the correlation between the reflectance and the gray level of the standard surfaces. These standard surfaces, which are employed for the manual analyzing process, corresponds to a known reflectance (0.525; 0.892; 1.236 and 1.688%).

The operating conditions have been optimized so as to obtain a sufficient dynamic of gray levels between the lowest reflectance and the highest reflectance.

The correlation between the reflectance and the mean gray level of the standard surfaces was determined so as to check the linearity of the relation and evaluate the dynamic level Ld (FIG. 5).

$$Ld = \frac{standard_{1.688} - standard_{0.525}}{GL_{1.688} - GL_{0.525}} = \frac{1.688 - 0.525}{183 - 97} = 0.0135$$

$GL_{1.688}$=mean gray level measured on the standard 1.688
$GL_{0.525}$=mean gray level measured on the standard 0.525

The mean dynamic level is equal to a reflectance of 0.0135% and is defined as the mean value of the reflectance for one unit of gray level.

The value of Ld determines the level of sensitivity of the measures. The standard established by the petrographs allows an absolute deviation of the reflectance of more or less 0.05% of the reflectance, this value corresponds to three gray levels, which is very satisfactory.

The linearity is not excellent for the values of reflectance between 0.892 and 1.688%, this domain of the reflectance of the vitrinite corresponds to the largest part of the coals employed.

Bearing in mind this remark, the relation between the two methods is achieved more strictly by applying the coefficients of correlation calculated for each interval of reflectance.

The operating conditions which permitted obtaining this result are optimum and are imposed for each coal analysis.

Tests carried out have revealed that the automatic process according to the invention for maceral analyses of coal achieves a considerable saving in the analyzing time by reducing it on average from four to one hour.

Further, the precision is distinctly improved, above all as concerns the maceral analysis.

The invention therefore permits effecting an improved control of the products for the purpose of contributing to the preparation of a coke of constant quality and to the evaluation of the cost price of the coal. Thus, considerable economic advantage results.

Lastly, it concerns a method which is not exacting for the operator, which in particular explains the improvement in the precision.

What is claimed is:

1. A process of maceral analysis of a sample of crushed coal coated with resin to determine a vitrinite content of the crushed coal, the process comprising the steps of:

scanning a surface of said sample with a microscope to obtain successive fields in said microscope;

measuring a reflectance of said vitrinite by forming a gray scale digitized image of said sample for each said field;

eliminating fields containing a quantity of resin higher than a given threshold according to the gray scale digitized image; and analyzing each said field not eliminated in the previous step according to the following process:
   a) determining a distribution of the gray levels;
   b) determining gradients of said gray levels;
   c) forming a binary image corresponding to zones of vitrinite by using said gradients;
   d) determining at least one of the distribution of said gray levels and densitometry values within said zones of vitrinite; and
   e) calculating values corresponding to said reflectance of said vitrinite.

2. The process according to claim 1, wherein said step of calculating values corresponding to said reflectance of said vitrinite comprises the step of determining a mean gray level for all of said zones of vitrinite of said sample.

3. The process according to claim 1, wherein said step of calculating values corresponding to said reflectance of said vitrinite comprises the step of determining a mean gray level of each said zone of vitrinite.

4. The process according to claim 1, further comprising the step of filtering said zones of vitrinite by size to eliminate zones of vitrinite which are small in size, before said step of determining the distribution of said gray levels.

5. The process according to claim 1, wherein said step of calculating values corresponding to said reflectance of said vitrinite uses said densitometry values.

6. The process according to claim 1, further comprising the step of correcting each image point by employing a reference image with a uniform gray value and a known reflectance value for each non-eliminated field.

7. The process according to claim 1, further comprising the step of adjusting a lighting of said microscope by using a surface having a known reflectance.

8. The process according to claim 1, further comprising the steps of calculating the vitrinite content, and analyzing said densitometry values without vitrinite to estimate the content of components of said sample other than said vitrinite, after said step of measuring said reflectance of said vitrinite.

* * * * *